United States Patent [19]

Shiotani et al.

[11] Patent Number: 5,290,910
[45] Date of Patent: Mar. 1, 1994

[54] POLYMER AND METHOD FOR PRODUCTION THEREOF

[75] Inventors: Takeshi Shiotani, Kakogawa; Genta Kobayashi, Takasago, both of Japan

[73] Assignee: Kanegafuchi Kagaku Kogyo Kabushiki Kaisha, Osaka, Japan

[21] Appl. No.: 921,137

[22] Filed: Jul. 29, 1992

[30] Foreign Application Priority Data

Aug. 3, 1991 [JP] Japan ............................ 3-217948

[51] Int. Cl.$^5$ .......................... C08G 63/06; C12P 7/62
[52] U.S. Cl. ................................ 528/361; 435/41; 435/135; 435/822; 435/874; 435/876; 528/354; 528/355; 528/491
[58] Field of Search ............... 528/354, 361, 355, 491; 435/135, 874, 875, 876, 41, 822

[56] References Cited

U.S. PATENT DOCUMENTS

| | | | |
|---|---|---|---|
| 4,800,162 | 1/1989 | Matson | 435/280 |
| 5,126,255 | 6/1992 | Anderson et al. | 435/135 |
| 5,138,029 | 8/1992 | Nishioka et al. | 528/354 |

FOREIGN PATENT DOCUMENTS 63-226291 9/1988 Japan .

OTHER PUBLICATIONS

G. Huisman et al., *Applied and Environmental Microbiology*, Aug. 1989, vol. 55, No. 8, pp. 1949–1954.
Arnulf–Timm and Alexander Steinbuchel, *Applied and Environmental Microbiology*, Nov. 1990, vol. 56, No. 11, pp. 3360–3367.
A. Anderson et al., *Int. J. Biol. Macromol.*, 1990, vol. 12, Apr. (1990), pp. 102–105.

Primary Examiner—John Kight, III
Assistant Examiner—Shelley A. Dodson
Attorney, Agent, or Firm—Birch, Stewart, Kolasch & Birch

[57] ABSTRACT

The present invention is directed to a copolymer containing a unit represented by Formula (1):

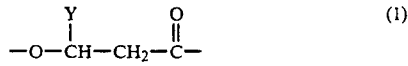

wherein Y represents a hydrocarbon residue having 1 to 13 carbon atoms which may have 1 to 4 double bonds. A method for production thereof comprises the steps of culturing microorganisms of the genus Pseudomonas under limitation of nutrients other than carbon sources using a medium containing long-chain fatty acids having 14 to 22 carbon atoms or lower alcohol esters thereof, or triglycerides comprising long-chain fatty acids having 14 to 22 carbon atoms as carbon sources; washing the bacterial cells after completion of cultivation; extracting the bacterial cells; and recovering a polyester from the extracts.

21 Claims, No Drawings

POLYMER AND METHOD FOR PRODUCTION THEREOF

FIELD OF THE INVENTION

The present invention relates to a novel polymer, a method for production thereof, and a microorganism used therefor, more specifically to a plastic-like polymer which undergoes microbial degradation in natural environments such as soil, rivers and seas, and a method for production thereof.

BACKGROUND OF THE INVENTION

A large number of microorganisms have been found to accumulate polyesters, as energy storage compounds, in the cells thereof. A typical example thereof is Poly-3-hydroxybutyrate [hereinafter simply referred to as P(3HB)], which is a homopolymer containing a monomer unit (3HB) represented by the following Formula (2).

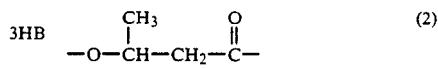

(2)

P(3HB) is a so-called biodegradable plastic, which undergoes biological degradation in natural environments; however, if viewed as a polymer material, it is insufficient for practical use because it is highly crystalline, hard and brittle.

As a means for overcoming these drawbacks, it has been proposed to incorporate a monomer unit which is structurally different from 3HB to compose the polyester. The methods based on this concept can be roughly divided into two groups as follows.

(1) According to Japanese Patent Laid-Open Nos. 150393/1982, 69225/1983, 269989/1988, 48821/1989 and 156320/1989, copolymer F(3HB-CO-3HV), containing 3-hydroxyvalerate (a monomer unit represented by Formula (3), simply referred to as 3HV) and 3HB, is obtained by culturing *Alcaligenes eutrophus,* a microorganism which essentially produces P(3HB), from a carboxylic acid having an odd number of carbon atoms, such as propionic acid or valeric acid, as a carbon source. Similarly, it is reported that copolymer P(3HB-CO-4HB), containing 4-hydroxybutyrate (a monomer unit represented by Formula (4), simply referred to as 4HB) and 3HB, is obtained from 4-hydroxybutyric acid or γ-butyrolactone, as a carbon source.

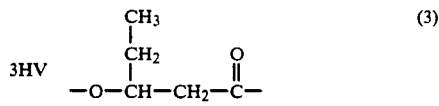

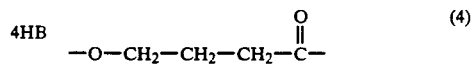

(2) According to Japanese Patent Laid-Open No. 226291/1988, it is reported that copolymer P(3HA), having 3-hydroxyalkanoate (simply referred to as 3HA) having 6 to 12 carbon atoms can be biosynthesized by *Pseudomonas oleovorans* ATCC29347, a hydrocarbon-utilizing bacterium, from alkanes. It as a carbon source. Here, to provide a clear representation of the relationship between each monomer unit structure and carbon number in 3HA, this monomer unit is referred to as a $C_x$ unit.

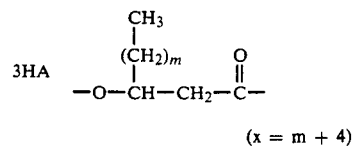

$(x = m + 4)$

According to the above-mentioned patent publications, 3HB is a $C_4$ unit and 3HV is a $C_5$ unit; *Pseudomonas oleovorans* is capable of intracellularly synthesizing and accumulating copolymers containing $C_6$ to $C_{12}$ units.

Also, "Applied and Environmental Microbiology, 1988, pages 1977-1982" states that the carbon source alkane should have at least 6 carbon atoms for *Pseudomonas oleovorans* to synthesize a polyester, and that units exceeding $C_{12}$ are not synthesized even if an alkane having a carbon number of 12 or more is added.

As stated above, two types of copolymer have been proposed. The copolymers of type 1 have a few methylene groups in the side chain thereof, and they are physically plastic-like polymers. The copolymers of type 2 have a large number of methylene groups in the side chain thereof, and they are physically gel-like polymers. The latter copolymers of type 2 have not been found practically valuable because their melting point (Tm) is about 40 to 60° C., which is too low to retain hardness.

The present inventors have conducted investigations in search of a microorganism which utilizes long-chain fatty acids having 14 to 22 carbon atoms or triglycerides comprising such long-chain fatty acids and which accumulates a polyester in the cells thereof, and have found a bacterial strain which accumulates a random polymer having extremely long chains of methylene groups (up to $C_{16}$ units) in the side chain thereof and also having a double bond in the side chain thereof. The present inventors have made further investigations based on this finding, and thus developed the present invention.

SUMMARY OF THE INVENTION

An object of the present invention is to provide a novel polymer which is a biodegradable plastic which undergoes enzymatic degradation by depolymerases, lipases and other enzymes found in natural environments, the polymer containing $C_4$ to $C_{16}$ units which may have a double bond in the side chain thereof being randomly arranged.

Another object of the present invention is to provide *Pseudomonas fluorescens* capable of synthesizing the polymer.

A further object of the present invention is to provide a method for production of the polymer using a microorganism of the genus Pseudomonas.

Accordingly, the present invention essentially relates to: (1) a polymer containing a unit represented by Formula (1):

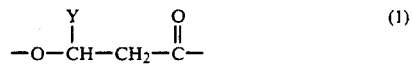

(1)

wherein Y represents a hydrocarbon residue having 1 to 13 carbon atoms which may have 1 to 4 double bonds, (2) *Pseudomonas fluorescens* capable of synthesizing the polymer described in (1) above, and (3) a method for production of the polymer described in (1) above using a microorganism of the genus Pseudomonas.

DETAILED DESCRIPTION OF THE INVENTION

With respect to Formula,(1), Y represents a hydrocarbon residue having 1 to 13 carbon atoms which may have 1 to 4 double bonds. Examples of such hydrocarbon residues include the following:

$CH_3—(CH_2)_7—CH=CH—CH_2—$,
$CH_3—(CH_2)_7—CH=CH—(CH_2)_3—$,
$CH_3—(CH_2)_4—CH=CH—$,
$CH_3—(CH_2)_4—CH=CH—(CH_2)_2—$,
$CH_3—(CH_2)_4—CH=CH—CH_2—CH=CH—CH_2—$,
$CH_3—(CH_2)_4—CH=CH—CH_2—CH=CH—(CH_2)_3—$,
$CH_3—CH_2—CH=CH—CH_2—$,
$CH_3—(CH_2—CH=CH)_2—$,
$CH_3—(CH_2—CH=CH)_2—(CH_2)_2—$,
$CH_3—(CH_2—CH=CH)_3—CH_2—$,
$CH_3—(CH_2—CH=CH)_3—(CH_2)_3—$,
and the like.

As stated above, the polymer of the present invention is 3HA containing a wide variety of monomer units ranging from $C_4$ to $C_{16}$, specifically a random polymer wherein the $C_4$ to $C_{16}$ units which may have a double bond in the side chain thereof are randomly arranged.

The microorganism of the present invention is not subject to limitation, as long as it is identified as *Pseudomonas fluorescens* capable of synthesizing the polymer as described above. The bacteriological characteristics of *Pseudomonas fluorescens* FA-031 are shown in Table 1.

TABLE 1

Bacteriological Characteristics of *Pseudomonas fluorescens* FA-031

| Test Items | Test Results |
| --- | --- |
| Morphology | Bacillus Rods |
| Gram Stain | − |
| Spore | − |
| Motility | + |
| Flagellar Number | >1 |
| Oxidase | + |
| Catalase | + |
| OF | 0 |
| PHB Accumulation | − |
| Production of Fluorescent Pigments | + |
| Arginine Dihydrolase | + |
| Growth at 41° C. | − |
| Denitrification Reaction | − |
| Nitrate Reduction | − |
| Gelatin Liquefaction | + |
| Starch Hydrolysis | − |
| Levan Formation from Sucrose | + |
| Lecithinase (Egg Yolk) | + |
| Lipase (Tween 80 Hydrolysis) | + |
| Utilization of: | |
| D-Alanine | + |
| meso-Inositol | − |
| Ethanol | − |
| Glucose | + |
| Geraniol | − |
| Trehalose | + |
| Propylene Glycol | − |

The FA-031 strain, an example of the microorganism of the present invention, was isolated from soil at Takasago-cho Miyamae-machi, Takasago-shi, Hyogo-ken, Japan, and has been deposited under accession number FERM BP 3433.

Isolation of the microorganism of the present invention followed by production of the polymer of the present invention can be achieved as follows.

(1) First, out of the Pseudomonas bacterial strains which grow on a selective medium containing long-chain fatty acids (carbon number of 14 to 22) as the only carbon source, (2) polyester-synthesizing bacterial strains are isolated by culture in a nitrogen-free medium containing long-chain fatty acids as a carbon source;

(3) the bacterial strains having a polymerase which act on long-chain 3-hydroxyacyl CoA are separated from the bacterial strains obtained in (2) above, and (4) polyester is synthesized by fermentation using the bacterial strains obtained in (3) above from naturally occurring saturated or variously unsaturated long-chain fatty acids as a carbon source under nitrogen source limitation.

Carbon sources which can be used herein are long-chain fatty acids having 14 to 22 carbon atoms or lower alcohol esters thereof, or triglycerides comprising long-chain fatty acids having 14 to 22 carbon atoms. Examples of long-chain fatty acids having 14 to 22 carbon atoms which can be used advantageously include oleic acid, linoleic acid and α-linolenic acid. Vegetable oils or animal oils comprising long-chain fatty acids having 14 to 22 carbon atoms can also be used.

For example, when the microorganism is allowed to synthesize polyester from oleic acid, an unsaturated fatty acid having 18 carbon atoms and a double bond at 9- position, as a carbon source, a polymer having a double bond in the side chain in each of the $C_{14}$ and $C_{16}$ units is obtained.

When the microorganism is allowed to synthesize polyester from an unsaturated fatty acid having 18 carbon atoms as a carbon source such as linoleic acid (having a double bond at each of 9- and 12-positions) or α-linolenic acid (having a double bond at each of the 9-, 12- and 15-positions), a polymer having a double bond in the side chain, for example, in each of the $C_{10}$, $C_{12}$, $C_{14}$ and $C_{16}$ units for linoleic acid, or in each of the $C_8$, $C_{10}$, $C_{12}$, $C_{14}$ and $C_{16}$ units for α-linolenic acid, is obtained. However, when linoleic acid is used as a carbon source, the $C_{10}$ unit is almost saturated hydroxy acid.

On the other hand, when stearic acid, a saturated fatty acid having 18 carbon atoms, is used as a carbon source, all the units of the polymer obtained are saturated units (with no double bond).

As stated above, according to the method for production of the present invention, a polymer having long-chain methylene groups in the side chain thereof or a polyester having an unsaturated unit containing a double bond in the polymer side chain can be synthesized by fermentation using naturally occurring oils and fats.

Based on these findings, it can be presumed that when a microorganism of the genus Pseudomonas is used for the method for production of the present invention, 3-hydroxyacyl CoA, an intermediate metabolite for β-oxidation of fatty acids, is converted to a monomer unit of the polyester by the polymerase.

Meantime, as described in Japanese Patent Laid-Open No. 226291/1988, Witholt synthesized by fermentation P(3HA) containing $C_6$ to $C_{12}$ units by culturing *Pseudomonas oleovorans* from n-alkanes as a carbon source, wherein oleic acid or linoleic acid was also used as a carbon source. However, even when these fatty acids were used, the polyester obtained was P(3HA) containing $C_6$ to $C_{12}$ units, and P(3HA) containing $C_4$ to $C_{16}$ units as in the present invention could not be obtained.

Also, as described in "Applied and Environmental Microbiology, Vol. 56, No. 11, 1990," Schlegel et al. obtained the polyesters synthesized by fluorescent pseudomonads from octanoate as a carbon source, which yielded P(3HA) containing $C_6$ to $C_{12}$ units as well.

These findings indicate that P(3HA) containing $C_4$ to $C_{16}$ units is obtained by culturing a bacterial strain having a polymerase with high affinity for long-chain 3-hydroxyacyl CoA from a long-chain fatty acid as a carbon source, and that this cannot be achieved by any method other than the method of the present invention.

Although the polyester synthesized by fermentation using the microorganism of the present invention can easily be obtained by culturing the microorganism under nitrogen source limitation as known generally, the desired polyester can also be synthesized even under limitation of essential nutrients other than carbon sources, such as phosphorus, minerals and vitamins.

In this case, fermentation synthesis of the polyester is often carried out in two stages, since the growth of bacterial cells is suppressed under nitrogen-free conditions. The first stage is aimed at the growth of the bacterial cells, wherein the microorganism is cultured under nutrient-rich conditions. In this case, not only fatty acids but also any carbon sources can be used optionally, as long as they can be utilized, since the bacterial cells show almost no polyester synthesis.

In the second stage, the bacterial cells grown in the first stage are washed and recovered, after which they are cultured in a newly added carbon source to synthesize the polyester. Therefore, the culturing conditions in the second stage are important. The carbon source added in the second stage is a starting material for the polyester synthesis; the structure of this carbon source determines the structure of the polyester. Thus, the carbon source used in the present invention means the carbon source added in this second stage. At the same time, the nitrogen source is also limited. In this stage, the C/N ratio is preferably not less than 7; polyester induction is possible even when the nitrogen source is not added. If the C/N ratio is less than 7, the carbon source is consumed for energy metabolism for the growth of the bacterial cells and for synthesis of bacterial cell components, which reduces the amount of carbon source used for polyester synthesis, and thus considerably lowers polyester yield.

Usual culturing conditions for the second stage are a PH of 6 to 8, a temperature of 25° to 35° C., an air flow rate of 0.5 to 2 vvm, and a cultivation time of 24 to 48 hours.

As carbon sources, fatty acids having 14 to 22 carbon atoms, such as palmitic acid, stearic acid, oleic acid, linoleic acid and a -linolenic acid, and lower alcohol esters thereof can be used. Natural oils and fats, specifically vegetable oils such as corn oil, safflower oil, sunflower oil, olive oil, soybean oil, rapeseed oil, palm oil and coconut oil, and animal oils such as fish oil, whale oil, lard and beef tallow can also be used. It is also possible to prepare a mixture of these carbon sources and use it to optionally control the composition of the polyesters.

Recovery of the polymer accumulated in the bacterial cells can be achieved by a conventional method. For example after completion of cultivation, the bacterial cells are washed with distilled water, methanol, etc., and then subjected to centrifugation, filtration and other procedures to remove the cells, after which methanol is added to the extract to precipitate and recover the polymer.

The polymer of the present invention, F(3HA), is a biodegradable plastic which undergoes enzymatic degradation by depolymerases, lipases and other enzymes in the natural environment. These enzymes break ester bonds in the main chain to lower the molecular weight, but the side chain structure is not a site directly involved in degradation, although it affects the rate of degradation to some degree.

Accordingly, it is possible to use the reaction site in the side chain of the polymer of the present invention, if any, to bind, for example, a pharmaceutical component or bioactive substance, with the side chain, and use the resulting conjugate as a base for sustained-release action in parallel with degradation of the main chain. Because the double bonds in the side chain can be replaced with highly reactive aldehyde groups by ozonic decomposition, the number of side chains having a double bond determines the rate of sustained release.

Because the method for production of the present invention makes it possible to easily adjust the number of side chains having a double bond by controlling the degree of saturation of long-chain fatty acids, the starting material for polyester synthesis, it is useful in obtaining random polymers for various purposes.

EXAMPLES

The present invention is hereinafter described in more detail by means of the following examples, which are not to be construed as limitative.

Example 1

The following medium composition for screening, containing oleic acid as the only carbon source, was diluted with water to yield a 1 liter of medium (pH 7.0) for microbial screening.

| | |
|---|---|
| Oleic Acid | 10 g |
| $NH_4NO_3$ | 5 g |
| $KH_2PO_4$ | 1.5 g |
| $K_2HPO_4$ | 1.5 g |
| $MgSO_4.7H_2O$ | 0.25 g |
| Yeast Extract | 0.1 g |
| Tween 20 | 0.5 g |

A soil suspension was subjected to shaking culture at 30° C. for 24 to 48 hours. 466 strains that utilized oleic acid were isolated on plate culture containing oleic acid as a carbon source. Next, these strains were cultured at 30° C. for 48 hours using the same medium as above except that it contained no $NH_4NO_3$. Bacterial cells were examined by phase difference microscopy, and 79 strains which form granules in the cells thereof were isolated. Next, the bacterial cells of these 79 strains were lyophilized and then subjected to extraction with chloroform at 50° C. for 2 hours, after which methanol was added in an amount 5 to 10 times the amount of chloroform, and the precipitate (polyester) was recovered and dried.

The precipitate thus, obtained was subjected to methanolysis under acidic conditions with sulfuric acid and then subjected to gas chromatography to identify it as a monomer unit of a polyester, and to examine the composition of the polyester.

As a result, 27 strains proved to synthesize P(3HA) containing $C_4$ to $C_{16}$ units by fermentation. One of them, identified as *Pseudomonas fluorescens* FA-031, has been deposited under accession number of FERM BP 3433.

Example 2

*Pseudomonas fluorescens* FA-031 was subjected to shaking culture at 30° C. for 48 hours using a medium prepared by adding water to the following medium composition to make a total quantity of 1 liter (pH 7.0).

| | |
|---|---|
| Meat Extract | 5 g |
| Peptone | 5 g |
| Yeast Extract | 2 g |
| $KH_2PO_4$ | 1.5 g |
| $K_2HPO_4$ | 1.5 g |
| $MgSO_4.7H_2O$ | 0.1 g |

After completion of cultivation, the culture broth was centrifuged and bacterial cells were recovered, the entire quantities of which were transferred into a medium prepared by adding water to the following medium composition to make a total quantity of I liter (pH 7.0), followed by shaking culture at 30° C. for 24 hours;

| | |
|---|---|
| Oleic Acid | 10 g |
| $KH_2PO_4$ | 1.5 g |
| $K_2HPO_4$ | 1.5 g |
| $MgSO_4.7H_2O$ | 0.25 g |
| Tween 85 | 0.5 g |

After completion of cultivation, bacterial cells were washed with distilled water and methanol and then dried under reduced pressure to yield dry cells, which were extracted with chloroform at 50° C. for 2 hours. After cell removal, a 10-fold amount of methanol was added to the chloroform extract to precipitate and recover polyester.

The resulting polyester was subjected to methanolysis at 110° C. for 140 minutes under acidic conditions with sulfuric acid to convert the monomer into the methyl ester, followed by capillary gas chromatographic analysis under increased temperature. The results are shown in Table 2.

TABLE 2

Monomer Units Using Fatty Acids Having Different Degrees of Unsaturation

| Example No. | Carbon* Source | $C_4$ S | $C_6$ S | $C_8$ S | $C_8$ U | $C_{10}$ S | $C_{10}$ U | $C_{12}$ S | $C_{12}$ U | $C_{14}$ S | $C_{14}$ U | $C_{16}$ S | $C_{16}$ U |
|---|---|---|---|---|---|---|---|---|---|---|---|---|---|
| 1 | Oleic Acid | 2 | 6 | 33 | 0 | 31 | 0 | 14 | 0 | 0 | 12 | 0 | 2 |
| 3 | Linoleic Acid | 1 | 3 | 23 | 0 | 0 | 22 | 0 | 19 | 0 | 27 | 0 | 5 |
| 4 | Linolenic Acid | 1 | 4 | 0 | 24 | 0 | 25 | 0 | 15 | 0 | 22 | 0 | 4 |
| 5 | Stearic Acid | 1 | 5 | 35 | 0 | 37 | 0 | 18 | 0 | 3 | 0 | 1 | 0 |

Remarks
*S: Saturated bond. U: Unsaturated bond.

When oleic acid was used as a carbon source, the obtained polymer contained $C_4$ to $C_{16}$ units, having a double bond in each of the $C_{14}$ and $C_{16}$ units, while the other units were saturated. This finding suggests that while oleic acid is undergoing β-oxidation, the intermediate metabolite 3-hydroxyacyl CoA forms a polyester unit by the action of depolymerase. Thus, *Pseudomonas fluorescens* was found to carry out polyester synthesis wherein fatty acid residues as carbon sources are formed in the side chain of the polyester.

Example 3

An experiment was conducted in the same manner as in Example 2 except that linoleic acid was used as a carbon source. As seen from the analytical results shown in Table 2, the polyester obtained contained $C_4$ to $C_{16}$ units, with a double bond noted in each of the $C_{10}$, $C_{12}$, $C_{14}$ and $C_{16}$ units. However, with respect to the $C_{10}$ unit, saturated $C_{10}$ peaks accounted for a large percentage, with only a few unsaturated peaks noted.

Example 4

An experiment was conducted in the same manner as in Example 2 except that a α-linolenic acid was used as a carbon source. As seen from the analytical results shown in Table 2, the polyester obtained contained $C_4$ to $C_{16}$ units, with a double bond noted in each of the $C_8$, $C_{10}$, $C_{12}$, $C_{14}$ and $C_{16}$ units.

Example 5

An experiment was conducted in the same manner as in Example 2 except that stearic acid was used as a carbon source. As seen from the analytical results shown in Table 2, the polyester obtained contained $C_4$ to $C_{16}$ units, and all of these units were saturated, containing no double bond.

Example 6

An experiment was conducted in the same manner as in Example 2 except that methylstearate was used as a carbon source. The analytical results were similar to those in Example 5.

Example 7

An experiment was conducted in the same manner as in Example 2 except that triolein (olive oil) was used as a carbon source. The analytical results were essentially the same as those in Example 2. Also, it was confirmed that similar results were obtained when a triglyceride was used in the place of the fatty acid.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A polymer comprising a group of repeating units represented by Formula (1):

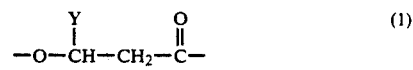

(1)

wherein Y represents a hydrocarbon residue having 12 to 13 carbon atoms which may have 1 to 4 double bonds, and wherein said group is a member selected from the group consisting of a unit having a carbon number of 4, a unit having a carbon number of 6, a unit having a carbon number of 8, a unit having a carbon number of 10, a unit having a carbon number of 12, a unit having a carbon number of 14, and a unit having a carbon number of 16.

2. A polymer according to claim 1, wherein said Y in Formula (1) represents a unit selected from the group consisting of $CH_3-(CH_2)_7-CH=CH-CH_2-$ and $CH_3-(CH_2)_7-CH=CH-(CH_2)_3-$.

3. The polymer according to claim 1, wherein said Y in Formula (1) represents a unit selected from the group consisting of $CH_3-(CH_2)_4-CH=CH-$, $CH_3-(CH_2)_4-CH=CH-(CH_2)_2-$, $CH_3-(CH_2)_4-CH=CH-CH_2-CH=CH-CH_2-$ and $CH_3-(CH_2)_4-CH=CH-CH_2-CH=CH-(CH_2)_3-$.

4. The polymer according to claim 1, wherein said Y in Formula (1) represents a unit selected from the group consisting of $CH_3-CH_2-CH=CH-CH_2-$, $CH_3-(CH_2-CH=CH)_2-$, $CH_3-(CH_2-CH=CH_2)_2-(CH_2)_2-$, $CH_3-(CH_2-CH=CH_3-CH_2-$ and $CH_3-(CH_2-CH=CH)_3-(CH_2)_3-$.

5. A *Pseudomonas fluorescens* capable of synthesizing a polymer containing a unit represented by Formula (1):

wherein Y represents a hydrocarbon residue having 1 to 13 carbon atoms which may have 1 to 4 double bonds.

6. A method for producing a polymer containing a unit represented by Formula (1):

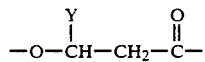

wherein Y represents a hydrocarbon residue having 1 to 13 carbon atoms which may have 1 to 4 double bonds comprising the steps of culturing a microorganism of the genus Pseudomonas under limitation of nutrients other than carbon sources using a medium containing at least one long-chain fatty acid having 14 to 22 carbon atoms or a lower alcohol ester thereof, or a triglyceride comprising a long-chain fatty acid having 14 to 22 carbon atoms as carbon atoms as carbon sources; washing the bacterial cells after completion of cultivation; extracting said bacterial cells; and recovering a polyester from the extract.

7. The method according to claim 6, wherein the carbon source is a member selected from the group consisting of oleic acid, linoleic acid, α-linolenic acid, a lower alcohol ester thereof, and a triglyceride comprising the acid thereof.

8. The method according to claim 6, wherein the carbon source is at least one vegetable oil or animal oil comprising long-chain fatty acids having 14 to 22 carbon atoms.

9. The *Pseudomonas fluorescens* according to claim 5, which is *Pseudomonas fluorescens FA*-031, FERM BP 3433.

10. The method according to claim 6, which is *Pseudomonas fluorescens* FA-031, FERM BP 3433.

11. The method according to claim 6, wherein said Pseudomonas is cultured in a medium containing oleic acid as a carbon source, thereby producing a polymer having a double bond in the side chain in each of the $C_{14}$ and $C_{16}$ units.

12. The method according to claim 6, wherein said Pseudomonas is cultured in a medium containing an unsaturated fatty acid having 18 carbon atoms as a carbon source, thereby producing a polymer having a double bond in the side chain.

13. The method according to claim 12, wherein said unsaturated fatty acid having 18 carbon atoms is a member selected from the group consisting of linoleic acid and α-linolenic acid, and said polymer has a double bond in each of the $C_{10}$, $C_{12}$, $C_{14}$, and $C_{16}$ units in the case of linoleic acid, and said polymer has a double bond in each of the $C_8$, $C_{10}$, $C_{12}$, $C_{14}$, and $C_{16}$ units in the case of α-linolenic acid.

14. The method according to claim 6, wherein said Pseudomonas is cultured in a medium containing linoleic acid as a carbon source, thereby producing a polymer wherein the $C_{10}$ unit is almost saturated hydroxy acid.

15. The method according to claim 6, wherein said Pseudomonas is cultured in a medium containing stearic acid or methylstearate as a carbon source, thereby producing a polymer wherein all the units are saturated.

16. The method according to claim 6, wherein said nutrients other than carbon sources are selected from the group consisting of nitrogen, phosphorus, minerals, and vitamins.

17. The method according to claim 16, wherein said culturing under nitrogen limitation is carried out in a first stage wherein said Pseudomonas is cultured under nutrient-rich conditions, followed by a second stage wherein the Pseudomonas cells are washed and recovered, after which they are cultured in a medium containing a newly added carbon source which determines the structure of the synthesized polyester, in which the nitrogen source is limited such that the C/N ratio is not less than 7.

18. The method according to claim 17, wherein no nitrogen source is present during said second stage of culturing.

19. The method according to claim 18, wherein the pH is 6 to 8, the temperature is 25° to 35° C., the rate of air flow is 0.5 to 2 vvm, and the cultivation time is 24 to 48 hours during said second stage of culturing.

20. The method according to claim 8, wherein said vegetable oil is a member selected from the group consisting of corn oil, safflower oil, sunflower oil, olive oil, soybean oil, rapeseed oil, palm oil, and coconut oil, and said animal oil is a member selected from the group consisting of fish oil, whale oil, lard, and beef tallow.

21. The method according to claim 6, wherein said long-chain fatty acids having 14 to 22 carbon atoms are selected from the group consisting of palmitic acid, stearic acid, oleic acid, linoleic acid, and α-linolenic acid.

* * * * *